US009555141B2

(12) United States Patent
Samadpour

(10) Patent No.: US 9,555,141 B2
(45) **Date of Patent: *Jan. 31, 2017**

(54) ADHERENT ANTIMICROBIAL BARRIER AND SANITIZING AGENT

(75) Inventor: Mansour Samadpour, Seattle, WA (US)

(73) Assignee: Institute For Environmental Health, Inc., Lake Forest Park, WA (US)

( * ) Notice: Subject to any disclaimer, the term of this patent is extended or adjusted under 35 U.S.C. 154(b) by 60 days.

This patent is subject to a terminal disclaimer.

(21) Appl. No.: 13/551,048

(22) Filed: Jul. 17, 2012

(65) Prior Publication Data

US 2013/0017186 A1 Jan. 17, 2013

Related U.S. Application Data

(63) Continuation of application No. 10/584,105, filed as application No. PCT/US2004/043253 on Dec. 22, 2004, now Pat. No. 8,226,888.

(Continued)

(51) Int. Cl.
*A61L 2/18* (2006.01)
*A61L 2/00* (2006.01)
(Continued)

(52) U.S. Cl.
CPC ................ *A61L 2/04* (2013.01); *A01N 25/24* (2013.01); *A01N 37/36* (2013.01); *A61L 2/16* (2013.01)

(58) Field of Classification Search
CPC ..................................................... A01N 25/24
(Continued)

(56) References Cited

U.S. PATENT DOCUMENTS 5,846,594 A 12/1998 Zimmerman
6,294,186 B1 * 9/2001 Beerse et al. ................ 424/405
(Continued)

OTHER PUBLICATIONS

International Search Report mailed Apr. 18, 2005, in International Patent Application No. PCT/US2004/043253, filed Dec. 22, 2004, 1 page.

*Primary Examiner* — Kevin Joyner
(74) *Attorney, Agent, or Firm* — Barry L. Davison, J.D.; Davis Wright Tremaine LLP

(57) ABSTRACT

Provided are viscous and adherent food-safe antimicrobial compositions, and methods for using same in the immediate and residual decontamination of microbial-contaminated substrate surfaces, in reducing or precluding cutting implement-mediated transfer of surface contamination during cutting operations in the food industry, and for reducing or preventing transfer of contamination from contaminated surfaces in the food and pharmaceutical industries. Adherent antimicrobial protective layers are formed on substrate surfaces (e.g., processing equipment and utensils), providing a barrier (e.g., chemical and/or physical) to the passage or transport of microbial contamination between and among surfaces. The adherent formulations confer residual decontaminating activity, providing for prolonged killing of associated microbial contamination, are preferably formulated and applied as a gel, syrup or foam, and preferably comprise materials that are 'generally-regarded-as-safe' (GRAS) in food products, obviating post-treatment removal prior to consumption. Preferably, the inventive formulations are heated to a temperature≥about 80° C. prior to application.

22 Claims, 1 Drawing Sheet

A

EtBr-Syrup Formulation

B

EtBr-Syrup Formulation

Related U.S. Application Data

(60) Provisional application No. 60/531,321, filed on Dec. 22, 2003.

(51) Int. Cl.

| | |
|---|---|
| ***A61L 2/04*** | (2006.01) |
| ***A01N 25/24*** | (2006.01) |
| ***A01N 37/36*** | (2006.01) |
| ***A61L 2/16*** | (2006.01) |

(58) Field of Classification Search
USPC ........................................................ 422/28, 37
See application file for complete search history.

(56) References Cited

U.S. PATENT DOCUMENTS

| | | | | |
|---|---|---|---|---|
| 6,387,977 | B1 * | 5/2002 | Sawhney et al. | 522/184 |
| 6,635,676 | B2 * | 10/2003 | Baker et al. | 514/642 |
| 2003/0100254 | A1 * | 5/2003 | Iwai | 452/173 |

* cited by examiner

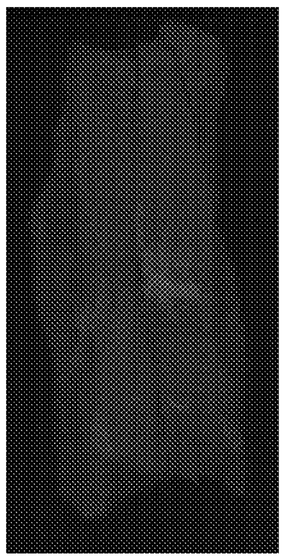
A
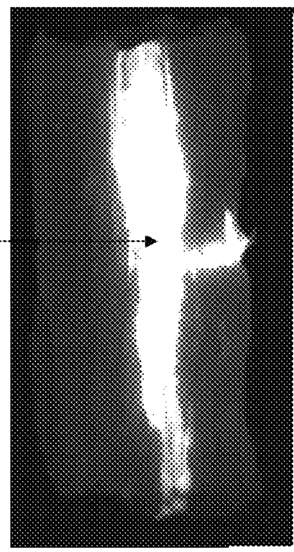
EtBr-Syrup Formulation
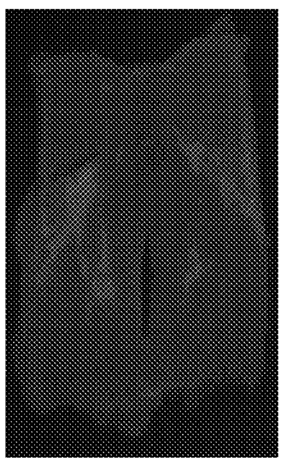
B
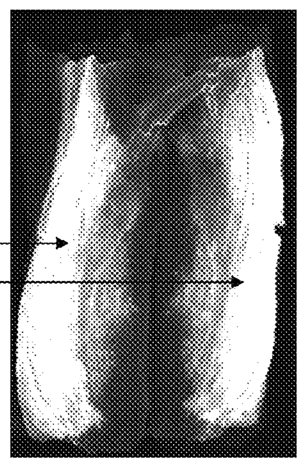
EtBr-Syrup Formulation

ADHERENT ANTIMICROBIAL BARRIER AND SANITIZING AGENT

CROSS REFERENCE TO RELATED APPLICATIONS

This application is a continuation of U.S. patent application Ser. No. 10/584,105 filed 21 Aug. 2007 (to issue as U.S. Pat. No. 8,226,888 on 24 Jul. 2012) and entitled "ADHERENT ANTIMICROBIAL BARRIER AND SANITIZING AGENT," which is the U.S. nationalization of PCT/US2004/043253 filed 22 Dec. 2004 and entitled "ADHERENT ANTIMICROBIAL BARRIER AND SANITIZING AGENT," which claims the benefit of priority to U.S. Provisional Application No. 60/531,321, filed 22 Dec. 2003 and entitled "ADHERENT KNIFE SANITIZER," all of which are incorporated by reference herein in their entirety.

FIELD OF THE INVENTION

The present invention relates generally to viscous, food-safe antimicrobial compositions and to methods for using same in decontaminating (e.g., immediate and residual) surfaces, and in forming an adherent protective layer on substrate surfaces (e.g., processing equipment and utensils) to provide a barrier to the passage of microbial contamination between and among surfaces contacted by, or in communication with a microbial-contaminated substrate surface.

BACKGROUND OF THE INVENTION

The presence of microbial contaminants that jeopardize product safety is a major problem in the food industry. Surface contamination of raw materials, product contact surfaces, and non-product contact surfaces are substantial challenges in the production of safe wholesome foods. Current sanitation practices involve preoperational cleaning and sanitation which does not confer residual sanitation properties to the surfaces. A number of liquid sanitization agents have been developed and are used during processing, most of which run off and have short-term effects.

An instructive example of issues relating to contaminated product surfaces is the meat packing industry, which at times represents a relatively extreme case involving gross levels of contamination. Microbiological loads on external surfaces of cattle are, based on various art-recognized studies, one of the primary sources of bacterial contamination of the derivative meat products. Therefore, lowering bacterial population densities on the surface of hides and carcass, and minimizing the transfer of contaminants could greatly reduce transfer of surface contamination (e.g., from contaminated hides) to the final product.

Various precautions and treatments have been applied to reduce bacterial contaminants on carcass surfaces; however, none can insure complete decimation of the microorganisms, or effectively preclude surface transfer of residual contamination. While decontamination interventions have been designed for preventing, reducing, or eliminating microbial contamination in the meat industry, the efforts have been focused on Good Manufacturing Practices and Sanitation Standard Operating Procedures for controlling microbial contamination of equipment and utensils used in processing, and decontamination treatments for controlling microbial contamination on the meat surfaces. The exterior surface and internal organs of live animals sent to slaughter are regarded as the primary source for introducing microbial contamination into processing facilities.

The harvest phase of meat production is perhaps the most challenging food production process in terms of controlling microbial contamination and transfer thereof down the production line into final products. The process of sanitary dressing of animals involves a number of steps in which implements used for the separation of hide from the carcass may become contaminated from the hide, and subsequently transfer the contamination to other surfaces on or within the carcass. The transfer of such contaminants is usually from microbial-contaminated hide to deep inside the carcass via cuts performed by hide-contaminated knives.

Currently, in the practice of 'dehiding' or general carcass fabrication, the cutting blade or other implements are decontaminated by dipping into hot water (>180° F.). When this step is done correctly, however, it ensures only the cleanliness of the implements prior to use. In practice, the implements often touch contaminated surfaces (e.g., the hide) during the 'dehiding' process. Microbes on the hide are thus inadvertently transferred from the hide to the carcass by means of the cutting implement. Another mechanism of transfer is by workers contacting the hide and subsequently touching another part of the carcass. Additional means of contaminant transfer include direct contact between the contaminated surface of the hide and areas of the exposed carcass, airborne transfer of contaminants, and contacts between product and non-product surfaces. Likewise, during the manufacturing of retail cuts, 'primals' and 'subprimals' are cut into smaller portions, and surface contamination is transferred through implements and product contact areas to the final product.

Contamination transfer issues also exist in the other segments of the food industry. In fish processing, similar problems occur during the cleaning and filleting operations. In the production of ready-to-eat food products, contamination travels from the raw processing areas to the final production areas and to the products primarily because the surfaces and the implements do not have residual antimicrobial components on them to prevent/reduce contamination.

Therefore, there is a pronounced need in the art to devise antimicrobial intervention strategies that can act as a barrier to prevent the transfer of bacterial contaminants from one surface to another during the preparation of foods, pharmaceuticals and other items which require asepsis or low bio-burden.

BRIEF DESCRIPTION OF THE DRAWINGS

FIGS. 1A and 1B show a top view (A; left), and exposed surfaces (B; right) of meat cut using a blade dipped in water, or in Ethidium Bromide-containing syrup formulated according to preferred aspects of the present invention. The results demonstrate the sacrificial protective barrier aspect of the inventive adherent antimicrobial formulations with respect to the exemplary use of an implement (i.e., a knife) of a type typically used in meat processing facilities for cutting through portions of meat.

SUMMARY OF THE INVENTION

Aspects of the present invention provide antimicrobial solutions or mixtures in, for example, viscous gel, syrup or foam forms. Preferably, the inventive formulations comprise food-grade materials and can be used directly on foods and food product contact surfaces. In preferred aspects, the viscosity of the solution contributes to adherence and barrier/sealant properties, while factors such as low or high pH, temperature, and/or active sanitizing molecules, act as decontaminants. The invention has utility in the application of barrier formulations to any appropriate surfaces encountered in, for example, the food or pharmaceutical product industry that contact or that may come into contact with the products. The antimicrobial barrier is formulated as, for example, a gel, syrup or foam, to possess the desired physical properties by using a combination of ingredients as described herein below. The specific formulation may vary depending on the type of application.

Upon application, a layer of the formulation (e.g., in gel or syrup form) covers the surface/implement/product. This layer not only sanitizes the surface, but also imparts residual effects for as long as the layer is present. This action prevents any microbial contaminants covered by the formulation from transfer to other surfaces, or to underlying areas. The surface is covered with the formulation, and prolonged adherence of the solution to the implement provides residual disinfecting properties. This is especially important if the surface in question is that of a knife used in food processing, where deep cuts may result in deposition of microbes in inaccessible layers. An equivalent foam formulation will form a protective layer when sprayed onto the surface of interest, and as such will eliminate the direct or indirect transfer of contaminants. Additional uses of the inventive formulations in the food industry include use in sanitizing implements that are used to handle ready-to-eat products during last stages of processing, and generally use anywhere where residual antimicrobial property is desired.

In preferred forms, the invention comprises viscous formulations of, for example gels, syrups or foams, which comprise 'generally-regarded-as-safe' (GRAS) ingredients that possess antimicrobial properties. The antimicrobial aspect of the formulation comprises, for example, acidic or basic compounds, chlorine or oxygen-based disinfectants, and with or without the addition of alcohols. An example of an inventive product formulation includes use of lactic acid as disinfectant (e.g., at pH 1.5 to 2.0), and pectin as a gelling/thickening agent.

Preferably, the inventive formulations comprise a GRAS agent for use in food products to confer the property of high viscosity. Preferred gelling/thickening agents include, but are not limited to: pectin, methylated pectin, gelatin, hydrosylated gelatin, agar, cornstarch, cross-linked starch, depolymerized starch, gelling vegetable protein product, sodium alginate, carrageenan, and combinations thereof.

Preferably, the inventive formulations comprise a GRAS agent for use in food products that conveys antimicrobial properties. Preferred agents include, but are not limited to: organic acids such as acetic, citric, and lactic acid; acidified calcium sulfate; acidified sodium chlorite; peracetic acid and other peroxyacetic acids and/or mixtures; percarbonates, ammonium hydroxide, quaternary ammonium salts, cetylpyridinium chloride, polyphosphates, glycolic acid, sodium metasilicate, trisodium phosphate, enzymes such as lysozyme, protease, lipase and phospholipase, alcohols such as ethanol and isopropoanol, and combinations thereof.

Preferably, when used as a foam application the invention incorporates a GRAS agent for use in food products which conveys emulsifying and foam stabilization properties. The following agents are preferred but are not limited to: calcium lactate, lecithin, and glycerol.

Preferably, when used as a foam application, the invention incorporates a GRAS agent for use in food products that conveys surfactant properties. Preferred agents include, but are not limited to: sodium lauryl sulfate, Tween 20, 40, 60, and 80, and combinations thereof.

Specific aspects provide a method of reducing or preventing transfer of contamination from a contaminated surface; comprising coating a contaminated surface or a portion thereof with an adherent antimicrobial barrier composition, comprising: from about 0.1 to about 25% (wt) of a gelling or thickening agent; from about 0.1 to about 10% (wt) of an emulsifier or stabilizer; from about 0.05 to about 10% (wt) of a surfactant; and an antimicrobial agent, whereby transfer of contamination from the surface is reduced or precluded. Preferably, the adherent antimicrobial barrier composition further comprises from about 0.1 to about 15% (wt), or about 1 to about 5% (wt), of one or more $C_{1-10}$ alcohols. Preferably, the adherent antimicrobial barrier composition is heated to at least 80° C. prior to application.

Additional aspects provide a method of reducing or precluding transfer of surface contamination during cutting operations, comprising: coating, prior to cutting through a target surface, at least one of: a cutting implement or a portion thereof; and the target surface or a portion thereof with an adherent sacrificial composition layer, wherein the sacrificial layer is partially transferable between the cutting implement and the target surface during cutting, whereby a protective layer is provided to the cutting implement surface while cutting through the target surface. Preferably, the adherent sacrificial composition comprises at least one agent selected from the group consisting of: from about 0.1 to about 25% (wt) of a gelling or thickening agent; from about 0.1 to about 10% (wt) of an emulsifier or stabilizer; from about 0.05 to about 10% (wt) of a surfactant; and an antimicrobial agent. Preferably, the adherent sacrificial composition further comprises from about 0.1 to about 15% (wt), or about 1 to about 5% (wt), of one or more $C_{1-10}$ alcohols. Preferably, the adherent sacrificial composition is heated to at least 80° C. prior to application.

Further aspects provide an antimicrobial barrier composition, comprising: from about 0.1 to about 25% (wt) of a gelling or thickening agent; from about 0.1 to about 10% (wt) of an emulsifier or stabilizer; from about 0.05 to about 10% (wt) of a surfactant; and an antimicrobial agent. Preferably, the antimicrobial barrier composition further comprises from about 0.1 to about 15% (wt), or about 1 to about 5% (wt), of one or more $C_{1-10}$ alcohols. Preferably, the gelling or thickening agent is present in an amount selected from the group consisting of from about 0.1 to about 4% (wt), from about 5 to about 15% (wt), and about 2.5% (wt), and is selected from the group consisting of pectin, methylated pectin, gelatin, hydrosylated gelatin, agar, cornstarch, cross-linked starch, depolymerized starch, gelling vegetable protein product, sodium alginate, carrageenan, and combinations thereof. Preferably, the emulsifier or stabilizer is present in an amount selected from the group consisting of from about 0.1 to about 1% (wt), from about 1 to about 5% (wt), and about 0.2% (wt), and is selected from the group consisting of calcium lactate, lecithin, glycerol, and combinations thereof. Preferably, the surfactant is present in an amount selected from the group consisting of from about 0.05 to about 0.5% (wt), from about 1 to about 5% (wt), and about 0.2% (wt), and is selected from the group consisting of sodium lauryl sulfate, Tween 20, 40, 60, and 80, and combinations thereof. Preferably, the antimicrobial agent is at least one of an acidic agent and a basic agent, present in an amount selected from the group consisting of from about 0.1 to about 15% (wt), from about 1 to about 5% (wt), and about 2% (wt), suitable to impart a pH of less than about 3, or greater than about 10, and is selected from the group consisting of acetic acid, citric acid, and lactic acid, acidified calcium sulfate, acidified sodium chlorite, peracetic acids, percarbonates, ammonium hydroxide, quaternary ammonium salts, cetylpyridinium chloride, polyphosphates, glycolic acid, sodium metasilicate, trisodium phosphate, and combinations thereof. Preferably, the antimicrobial agent is selected from the group consisting of proteases, lipases and phospholipases, alcohols, and combinations thereof. Preferably, the antimicrobial agent is heat. Preferably, the antimicrobial barrier composition is provided as a formulation selected from the group consisting of semi-solids, gels, liquids, syrups, aerosolized formulations, foams, colloidal suspensions, and combinations thereof.

DETAILED DESCRIPTION OF THE INVENTION

Antimicrobial barrier formulations are provided that, by virtue of adherent properties, have utility to seal off microbial contaminants, and eliminate contaminant transfer to other surfaces. The inventive formulations also confer residual antimicrobial property to surfaces (e.g., foods, equipment, production areas), and impart antimicrobial properties to surfaces to which they are applied. In particular aspects, the technology comprises an antimicrobial barrier that can translocate during use of formulation-coated implement and thus confer contaminant transfer protection to implements which are used in processing. The inventive formulations can also be applied to contaminated surfaces, such as hide, to cover the surface and exclude and disinfect contaminants. The inventive subject matter not only has utility for covering of utensils and equipment in the plant, but also in covering any surface where microbial contamination may be established and present a risk, the surfaces including, but not limited to post-mortem animal surfaces, plant floors, walls, conveyor belts, etc. Antimicrobial properties, for purposes of the present invention, are conferred by chemical (sanitizing agents) or physical (pH, oxidation, temperature) means.

In preferred embodiments, the invention provides formulations for use in food production areas as a direct or indirect antimicrobial barrier applied to food surfaces, or to food or pharmaceutical production surfaces, and which confers protection to the food or drugs being processed.

Accordingly, preferred aspects of the present invention provide an adherent liquid (low to high viscosity), gel, or foam formulation, comprising: (i) a food-grade gelling or thickening agent (e.g., preferably a GRAS compound approved as a direct food additive or food contact ingredient that will not affect the food and will have no adverse effect on humans upon ingestion; (ii) a food-grade emulsifying or foam stabilization agent (e.g., preferably a GRAS compound as described above); (iii) a food-grade surfactant (e.g., preferably a GRAS compound as described above); and, (iv) a food-grade acidic or basic agent to provide acidity or alkalinity (e.g., preferably a GRAS compound as described above).

Additional preferred aspects of the present invention provide an adherent liquid (low to high viscosity), gel, or foam formulation, comprising: (i) a food-grade gelling or thickening agent (e.g., preferably a GRAS compound as described above); (ii) a food-grade emulsifying or foam stabilization agent (e.g., preferably a GRAS compound as described above); (iii) a food-grade surfactant (e.g., preferably a GRAS compound as described above); and, (iv) a sanitizing agent (e.g., preferably a GRAS compound as described above).

Further aspects comprise application of heat or a heat source to elevate the temperature of the inventive adherent antimicrobial barrier formulations to >75° C. Such preferred heated embodiments comprise use of a highly viscous inventive formulation to obtain compositions (e.g., syrups) with significant heat retentive properties and sufficient adherence to be delivered as a hot solution to a desired surface.

The following non-limiting exemplary ingredients and formulations (TABLE 1) are provided to illustrate preferred aspects of the inventive antimicrobial barrier formulations:

TABLE 1

| Type of Ingredient | Ingredient | Form of Barrier |
|---|---|---|
| Gelling/ Thickening Agents | Pectin | Liquid, Gel, Foam |
| | Methylated Pectin | Liquid, Gel, Foam |
| | Gelatin | Liquid, Gel, Foam |
| | Hydrosylated Gelatin | Liquid, Gel, Foam |
| | Agar | Liquid, Gel, Foam |
| | Cornstarch | Liquid, Gel, Foam |
| | Cross-linked Starch | Liquid, Gel, Foam |
| | Depolymerized Starch | Liquid, Gel, Foam |
| | Vegetable/Animal Protein | Liquid, Gel, Foam |
| | Sodium Alginate | Liquid, Gel, Foam |
| | Carrageenan | Liquid, Gel, Foam |
| Sanitizing Agent | Organic Acids (acetic, citric, lactic) | Liquid, Gel, Foam |
| | Acidified Calcium Sulfate | Liquid, Gel, Foam |
| | Acidified Sodium Chlorite | Liquid, Gel, Foam |
| | Peracetic acid and mixtures thereof | Liquid, Gel, Foam |
| | Percarbonates | Liquid, Gel, Foam |
| | Ammonium Hydroxide | Liquid, Gel, Foam |
| | Quaternary Ammonium Salts | Liquid, Gel, Foam |
| | Cetylpyridinium Chloride | Liquid, Gel, Foam |
| | Polyphosphates | Liquid, Gel, Foam |
| | Glycolic Acid | Liquid, Gel, Foam |
| | Sodium Metasilicate | Liquid, Gel, Foam |
| | Trisodium Phosphate | Liquid, Gel, Foam |
| | Lysozyme | Liquid, Gel, Foam |
| | Lactoferrin | Liquid, Gel, Foam |
| Emulsifier/ Stabilizer | Calcium Lactate | Foam |
| | Lecithin | Foam |
| | Glycerol | Foam |
| Surfactants | Sodium Lauryl Sulfate | Foam |
| | Tween 20, 40, 60, 80 | Foam |

The following non-limiting examples (TABLE 2) further illustrate preferred inventive formulations:

TABLE 2

| Ingredients | Wt (%) |
|---|---|
| Gel Formulation #1 (pH 1.96) | |
| Pectin | 25 |
| Citric Acid | 2-5 |
| Water | 70-73 |
| Gel Formulation #2 (pH 1.6) | |
| Pectin | 16-33 |
| Lactic Acid | 5 |
| Water | 62-79 |
| Liquid (Syrup) Formulation #1 (pH 1.9) | |
| Pectin | 2.5 |
| Lactic Acid | 5 |
| Water | 92.5 |
| Liquid (Syrup) Formulation #2 (pH 2) | |
| Pectin | 1.5-3.0 |
| Gelatin | 0.5-1.5 |
| Lactic Acid | 5 |
| Water | 90.5-93.0 |
| Foam Formulation #1 (pH 2) | |
| Pectin | 0.75 |
| Gelatin | 2.5 |

TABLE 2-continued

| Ingredients | Wt (%) |
|---|---|
| Lactic Acid | 5 |
| Water | 91.5 |
| Foam Formulation #2 (pH 1.94) | |
| Pectin | 0.75 |
| Gelatin | 2.5 |
| Lactic Acid | 5 |
| Tween 80 | 1 |
| Water | 90.5 |

Preferred solid (e.g., gel) forms of the inventive antimicrobial barrier formulations comprise at least one agent selected from the group consisting of: from about 5 to about 25% (wt) of one or more gelling/thickening agents (preferably about 5 to about 15% (wt)); a sufficient amount of one or more acidic agents to produce a formulation pH lower than about 6 (preferably lower than about pH 3, and generally achieved with about 0.1 to about 15% (wt) acid agent, or preferably about 1 to about 5% (wt) acid agent); a sufficient amount of one or more alkaline agents to produce a pH higher than about 9 (preferably higher than about 10 and generally achieved with about 0.1 to about 15% (wt) basic agent); about 0.1 to about 15% (wt) of one or more sanitizing agents; and about 0.1 to about 15% (wt) (preferably about 1 to about 5% (wt)) of one or more $C_{1-10}$ alcohols. Preferably, the balance is water, or substantially water.

Preferred liquid (syrup) forms of the inventive antimicrobial barrier formulations comprise at least one agent selected from the group consisting of: about 0.5 to about 6% (wt) of one or more gelling/thickening agents (preferably about 1 to about 3.5% (wt)); a sufficient amount of one or more acidic agents to produce a pH lower than about 6 (preferably lower than about pH 3 and generally achieved with about 0.1 to about 15% (wt) acidic agent); sufficient amount of one or more alkaline agents to produce a pH higher than about 9 (preferably higher than about 10 and generally achieved with 0 to 15% (wt) basic agent); about 0.1 to about 1% (wt) of one or more sanitizing agents; and about 0.1 to 15% (wt) (preferably 1 to 5 wt-%) of one or more $C_{1-10}$ alcohols. Preferably, the balance is water, or substantially water.

Preferred aerosolized (foam) forms of the inventive antimicrobial barrier formulations comprise at least one agent selected from the group consisting of: about 0.5 to about 6% (wt) of one or more gelling/thickening agents (preferably about 1 to about 3.5 wt-%); a sufficient amount of one or more acid agents to produce a pH lower than about 6 (preferably lower than about pH 3 and generally achieved with about 0.1 to about 15% (wt) acidic agent); sufficient amount of one or more alkaline agents to produce a pH higher than about 9 (preferably higher than about 10 and generally achieved with about 0.1 to about 15% (wt) basic agent); about 0.1 to about 15% (wt) of one or more sanitizing agents; about 0.1 to about 10% (wt) (preferably about 1 to about 5 wt-%) of one or more surfactants; about 0.1 to about 10% (wt) (preferably about 1 to about 5% (wt)) of one or more emulsifies; and about 0.1 to about 15% (wt) (preferably about 1 to about 5% (wt)) of one or more $C_{1-10}$ alcohols; and, the balance water. Preferably, the balance is water, or substantially water.

In particularly preferred embodiments the inventive antimicrobial barrier formulations comprise at least one agent selected from the group consisting of: from about 0.1 to about 4% (wt) (preferably about 2.5% (wt)) of one or more gelling agents (e.g., Gelatin); from about 0.1 to about 1% (wt) (preferably about 0.2% (wt)) of one or more foam stabilizing agents; from about 0.05 to about 0.5% (wt) of one or more surfactants; from about 1 to about 5% (wt) of one or more acid, base or other sanitizing agents; and from about 2 to about 25% (wt) of one or more alcohols. Preferably, the balance is water, or substantially water.

EXAMPLE 1

This Example (TABLE 3) demonstrates the viscous nature of two solutions prepared with different concentrations of pectin (15 and 25%). The fluidity of viscous solutions formulated with 15 and 25% pectin and heated to 80° C. or left unheated (22° C.) was tested. Specifically, the heated or unheated solutions were drawn up into a 25 ml pipette and left to drain free of the solution. The time (in seconds) was measured to determine residence time of the various fluids in the pipette.

TABLE 3

Adherent properties of formulated liquid solutions containing various concentrations of pectin as the primary gelling/thickening agent

| % Pectin | Temperature (° C.) | Volume (ml) | pH | Time to Drain (s) |
|---|---|---|---|---|
| 0 (Water control) | 22 | 25 | 7.2 | 2.4 |
| 15 | 22 | 25 | 2.3 | 14.5 |
| 15 | 80 | 25 | 2.4 | 3.9 |
| 25 | 22 | 25 | 2.1 | 190.5 |
| 25 | 80 | 25 | 2.1 | 19.9 |

As shown by the data, the relative retention times were enhanced by relatively low pH and relatively low temperature.

EXAMPLE 2

This Example (TABLE 4) demonstrates the antimicrobial properties conferred by an exemplary liquid formulation composed of 5% lactic acid, 2.5% pectin, and 92.5% water. The disinfecting quality of the solution was tested on an aqueous culture of *Escherichia coli* biotype I. For the test the following ratios of a $10^5$ CFU/ml culture were prepared with the antimicrobial formulation: 9:1; 2:1; and, 1:1. The mixtures were left for 30 seconds after which time, serial dilutions were made and plated onto *Escherichia coli*/Coliform Petrifilms (3M; St. Paul, Minn.). Plates were incubated at 35° C. for 24 hours and counted to enumerate survivors.

Results. TABLE 4 indicates that at a ratio of 9:1 (Culture: Antimicrobial Barrier formulation), populations were not substantially reduced, while at a ratio of 2:1, populations were reduced by >4 log CFU/ml.

Although, the present Example does not provide a sanitizer as defined by the Environmental Protection Agency (i.e., 5 log reduction of bacterial suspension using 1 ml of culture with 9 ml of sanitizer), it does provide an exemplary sanitizing agent, indicated by the substantial reduction at lower dilution ratios, confirming the antimicrobial property of an exemplary low pH adherent formulation.

TABLE 4

| Survival (log CFU/ml) of *Escherichia coli* exposed to antimicrobial formulation consisting of 2.5% pectin, 5% lactic acid, and 92.5% water in a liquid phase. | | |
|---|---|---|
| *E. coli* Culture:Antimicrobial | Time of Exposure (s) | |
| Barrier Formulation (v/v) | 0 | 30 |
| 9:1 | 5.2 | 4.8 |
| 2:1 | 5.2 | <1 |
| 1:1 | 5.2 | <1 |

EXAMPLE 3

The Example (TABLE 5) demonstrates, according to preferred aspects of the present invention, the efficacy of the inventive barrier formulations in reducing or precluding bacterial contamination transferred by the surface of a stainless steel knife, which represents an implement typically used in a food processing operation. Specifically, the adherent antimicrobial barrier property of the inventive formulations was tested to determine the efficacy of said solutions to exclude bacterial contamination from food surfaces that may become contaminated during the use of implements (such as knives) in food processing. This Example models the operation of a knife in a 'dehiding' process of cattle in a beef operation.

In such operations, there is a high probability that the exterior of beef cattle will be covered with microbiologically-contaminated fecal material, presenting a risk of internalizing the contamination—to otherwise sterile underlying tissue during process cuts. The inventive viscous barrier solutions (e.g., gel, syrup or foam) have substantial utility in such processes by covering the knife blade and/or the exterior surface of the animal, thereby reducing or precluding inadvertent translocation of bacterial contamination by knife penetration to otherwise sterile underlying tissue.

Accordingly, to test the ability of the formulated solutions to act as a barrier to minimize bacterial transfer to meat tissue, various relevant scenarios were comparatively evaluated. The scenarios included: touching a knife surface to meat covered with a fecal inoculum and determining the amount of contamination transferred to the knife; touching a knife to a layer of inventive barrier foam formulation overlaying fecal inoculum on meat and determining the amount of contamination transferred to the knife; and touching a knife to a layer of inventive barrier syrup formulation overlaying fecal inoculum on meat and determining the amount of contamination transferred to the knife.

Additional scenarios, representing common and current industry practices were also comparatively evaluated: dipping a blade in 80° C. water, prior to touching a contaminated surfaces as described above; covering implements prior to contacting the contaminated surface; and covering the meat substrate (here representing the exterior surface of the animal).

Results. Table 5 shows that dipping knives into water (80° C.) before contacting the contaminated meat surface is not effective at preventing or reducing the transfer of surface contamination to the knife. By contrast, the use of inventive syrup or foam barrier formulations on the knife and/or on the substrate surface was substantially effective in preventing bacterial contamination of the blade surface from the contaminated meat surface.

Therefore, according to the present invention, modifications to the treatment of implements (e.g., knives typically used in the meat slaughtering industry) and/or substrate surfaces to include an adherent barrier substantially decreases the risk of transferring bacterial contamination to the knife and, thus, to subsequently contacted surfaces and/or underlying tissues.

TABLE 5

| Levels (mean log CFU/ml ± standard deviations) of bacterial contamination (determined on Aerobic Plate Count Petrifilm; 3M) on a knife surface contacted to meat inoculated with a fecal slurry containing $1 \times 10^4$ CFU/cm$^2$ *Escherichia coli*. | |
|---|---|
| Sample Description | Bacterial Populations |
| Knife touched to feces | 3.8 (0.2) |
| Knife touched to foam covering feces | 0.4 (0.8) |
| Knife touched to syrup covering feces | 0 (0) |
| Knife dipped in water and touched to feces | 3.3 (0.3) |
| Knife dipped in water and touched to foam covering feces | 0.1 (0.2) |
| Knife dipped in water and touched to syrup covering feces | 0.2 (0.5) |
| Knife dipped in water followed by syrup and touched to feces | 1.5 (1.3) |
| Knife dipped in water followed by syrup and touched to foam covering feces | 0 (0) |
| Knife dipped in water followed by syrup and touched to syrup covering feces | 0 (0) |

EXAMPLE 4

The following Example illustrates, according to the present invention, the principles involved in reducing or precluding carcass cutting implement-mediated (e.g., cutting knife-mediated) translocation of hide-born microbial contamination to interior carcass surfaces.

Specifically, FIG. 1 demonstrates the sacrificial protective barrier aspect of the inventive adherent antimicrobial formulations with respect to the use of an implement (i.e., a knife) of a type typically used in a meat processing facility for cutting through a portion of meat.

A knife was dipped in water per standard industry practice, or for comparison was dipped in an inventive liquid (syrup) formulation comprising 2.5% (wt) pectin and 5% (wt) lactic acid. The syrup was detectably laced with Ethidium Bromide (EtBr) and kept at 23° C. The dipped knife, in each case, was used to cut through a piece of meat having dimension of about 4×4×15 cm. After, the incision from the top of the meat through to the bottom, a photographic image of the meat was generated in a UV chamber to visualize the EtBr-containing syrup. The meat was then spread out around the cut to visualize the spread of the EtBr-containing syrup through the piece of meat to observe the ability of syrup to transfer with the blade through material based on its adherent properties.

The results show that the inventive adherent syrup formulation was delivered to, and sacrificially deposited onto contact surfaces thereby isolating potential surface contaminants from the passing blade during cutting. Significantly, as evident from the ethidium staining pattern, an adherent, residual non-sacrificed portion of the formulation transferred with the knife, providing a continuing protective layer to the knife for at least 3 cm through the 4 cm of meat.

According to preferred aspects of the present invention, the disclosed formulations have novel and substantial utility to reduce or preclude cutting implement-mediated transfer of surface contamination during cutting operations in the food and pharmaceutical industry, and for reducing or preventing transfer of contamination from a contaminated surface.

The invention claimed is:

1. A method of reducing or preventing transfer of microbial contamination to or from a surface being cut, comprising:
   - providing a surface to be cut;
   - providing a cutting implement;
   - coating the surface or a portion thereof, and coating the cutting implement or a portion thereof, with an adherent sacrificial antimicrobial barrier gel composition; and
   - cutting through the sacrificial layer on the surface with the cutting implement, wherein at least part of the adherent sacrificial antimicrobial barrier gel composition is transferred as a protective adherent layer between the surface and the cutting implement during cutting, and wherein transfer of microbial contamination to or from the surface is reduced or precluded.

2. The method of claim 1, further comprising, prior to coating, heating the adherent sacrificial antimicrobial barrier composition to a temperature equal to or greater than 80° C.

3. The method of claim 1, wherein the adherent sacrificial antimicrobial barrier gel composition is provided as a formulation selected from the group consisting of semi-solids, gels, liquids, syrups, aerosolized formulations, foams, colloidal suspensions, and combinations thereof.

4. The method of claim 1, wherein the adherent sacrificial antimicrobial barrier gel composition comprises at least one agent selected from the group consisting of: from about 0.1 to about 25% (wt) of a gelling or thickening agent; from about 0.1 to about 10% (wt) of an emulsifier or stabilizer; from about 0.05 to about 10% (wt) of a surfactant; and an antimicrobial agent.

5. The method of claim 4, wherein the adherent sacrificial antimicrobial barrier gel composition further comprises from about 0.1 to about 15% (wt), or about 1 to about 5% (wt), of one or more C1-10 alcohols.

6. The method of claim 4, wherein the gelling or thickening agent is present in an amount selected from the group consisting of from about 0.1 to about 4% (wt), from about 5 to about 15% (wt), and about 2.5% (wt), and is selected from the group consisting of pectin, methylated pectin, gelatin, hydrosylated gelatin, agar, cornstarch, cross-linked starch, depolymerized starch, gelling vegetable protein product, sodium alginate, carrageenan, and combinations thereof.

7. The method of claim 4, wherein the emulsifier or stabilizer is present in an amount selected from the group consisting of from about 0.1 to about 1% (wt), from about 1 to about 5% (wt), and about 0.2% (wt), and is selected from the group consisting of calcium lactate, lecithin, glycerol, and combinations thereof.

8. The method of claim 4, wherein the surfactant is present in an amount selected from the group consisting of from about 0.05 to about 0.5% (wt), from about 1 to about 5% (wt), and about 0.2% (wt), and is selected from the group consisting of sodium lauryl sulfate, Tween 20, 40, 60, and 80, and combinations thereof.

9. The method of claim 4, wherein the antimicrobial agent is at least one of an acidic agent and a basic agent, present in an amount selected from the group consisting of from about 0.1 to about 15% (wt), from about 1 to about 5% (wt), and about 2% (wt), suitable to impart a pH of less than about 3, or greater than about 10, and is selected from the group consisting of acetic acid, citric acid, and lactic acid, acidified calcium sulfate, acidified sodium chlorite, peracetic acids, percarbonates, ammonium hydroxide, quaternary ammonium salts, cetylpyridinium chloride, polyphosphates, glycolic acid, sodium metasilicate, trisodium phosphate, and combinations thereof.

10. The method of claim 4, wherein the antimicrobial agent is selected from the group consisting of proteases, lipases and phospholipases, alcohols, and combinations thereof.

11. The method of claim 4, wherein the antimicrobial agent is heat.

12. The method of claim 1, further comprising, prior to coating, heating the adherent sacrificial antimicrobial barrier composition to a temperature equal to or greater than 80° C.

13. The method of claim 1, wherein the adherent sacrificial antimicrobial barrier gel composition is provided as a formulation selected from the group consisting of semi-solids, gels, liquids, syrups, aerosolized formulations, foams, colloidal suspensions, and combinations thereof.

14. The method of claim 11, further comprising coating, prior to cutting through the target surface, the cutting implement or a portion thereof.

15. The method of claim 1 wherein the adherent sacrificial antimicrobial barrier gel composition, comprises:
   - from about 0.1 to about 25% (wt) of a gelling or thickening agent;
   - from about 0.1 to about 10% (wt) of an emulsifier or stabilizer;
   - from about 0.05 to about 10% (wt) of a surfactant; and
   - an antimicrobial agent.

16. The method of claim 15, wherein the adherent antimicrobial barrier gel composition further comprises from about 0.1 to about 15% (wt), or about 1 to about 5% (wt), of one or more $C_{1-10}$ alcohols.

17. The method of claim 15, wherein the gelling or thickening agent is present in an amount selected from the group consisting of from about 0.1 to about 4% (wt), from about 5 to about 15% (wt), and about 2.5% (wt), and is selected from the group consisting of pectin, methylated pectin, gelatin, hydrosylated gelatin, agar, cornstarch, cross-linked starch, depolymerized starch, gelling vegetable protein product, sodium alginate, carrageenan, and combinations thereof.

18. The method of claim 15, wherein the emulsifier or stabilizer is present in an amount selected from the group consisting of from about 0.1 to about 1% (wt), from about 1 to about 5% (wt), and about 0.2% (wt), and is selected from the group consisting of calcium lactate, lecithin, glycerol, and combinations thereof.

19. The method of claim 15, wherein the surfactant is present in an amount selected from the group consisting of from about 0.05 to about 0.5% (wt), from about 1 to about 5% (wt), and about 0.2% (wt), and is selected from the group consisting of sodium lauryl sulfate, Tween 20, 40, 60, and 80, and combinations thereof.

20. The method of claim 15, wherein the antimicrobial agent is at least one of an acidic agent and a basic agent, present in an amount selected from the group consisting of from about 0.1 to about 15% (wt), from about 1 to about 5% (wt), and about 2% (wt), suitable to impart a pH of less than about 3, or greater than about 10, and is selected from the group consisting of acetic acid, citric acid, and lactic acid, acidified calcium sulfate, acidified sodium chlorite, peracetic acids, percarbonates, ammonium hydroxide, quaternary ammonium salts, cetylpyridinium chloride, polyphosphates, glycolic acid, sodium metasilicate, trisodium phosphate, and combinations thereof.

21. The method of claim 15, wherein the antimicrobial agent is selected from the group consisting of proteases, lipases and phospholipases, alcohols, and combinations thereof.

22. The method of claim 15, wherein the antimicrobial agent is heat.

* * * * *